United States Patent [19]
Ito

[11] Patent Number: 5,305,736
[45] Date of Patent: Apr. 26, 1994

[54] DISTAL END PART OF ENDOSCOPE

[75] Inventor: Keiji Ito, Tokyo, Japan

[73] Assignee: Asahi Kogaku Kogyo Kabushiki Kaisha, Tokyo, Japan

[21] Appl. No.: 871,696

[22] Filed: Apr. 21, 1992

[30] Foreign Application Priority Data

Apr. 26, 1991 [JP] Japan .................................. 3-191339
May 14, 1991 [JP] Japan .................................. 3-206618

[51] Int. Cl.$^5$ .............................................. A61B 1/06
[52] U.S. Cl. ...................................................... 128/6
[58] Field of Search ................ 128/6, 4; 385/117, 119; 606/15

[56] References Cited

U.S. PATENT DOCUMENTS

| | | | |
|---|---|---|---|
| 3,664,730 | 5/1972 | Cardova | 385/119 X |
| 3,896,793 | 7/1975 | Mitsui et al. | 385/119 X |
| 4,576,147 | 3/1986 | Hashiguchi | 385/117 X |
| 4,773,396 | 9/1988 | Okazaki | 128/6 |
| 4,846,154 | 7/1989 | MacAnnally et al. | 385/117 X |
| 4,871,229 | 10/1989 | Tashiro | 385/117 |
| 4,942,867 | 7/1990 | Takahashi et al. | 128/6 |
| 4,944,287 | 7/1990 | Takahashi et al. | 128/4 |
| 4,971,035 | 11/1990 | Ito | 128/6 |
| 5,036,834 | 8/1991 | Sugiyama et al. | 128/6 |
| 5,190,028 | 3/1993 | Lafferty et al. | 385/117 X |

FOREIGN PATENT DOCUMENTS 52-52386  4/1977  Japan .
63-316013 12/1988  Japan .

OTHER PUBLICATIONS

English Abstract of Japanese Patent No. 63-316013.
English Abstract of Japanese Patent No. 52-52386.

Primary Examiner—Richard J. Apley
Assistant Examiner—Beverly A. Meindl
Attorney, Agent, or Firm—Sandler Greenblum & Bernstein

[57] ABSTRACT

A distal end part of an endoscope, which has an objective optical system arranged to face forwardly in a distal end block, and a solid-state imaging device disposed in the distal end block at a position where an observed image is formed by the objective optical system. The distal end part includes a light guide fiber bundle for illuminating an observation filed of view of the object optical system, and a bore that is provided in the distal end block with an angle of inclination so that the boar approaches an optical axis of the objective optical system at the forward end thereof. The distal end part further includes a straight pipe shorter than the objective optical system, which is inserted into the bore and rigidly secured thereto, with the straight pipe receiving an exit end portion of the light guide fiber bundle, and an illuminating lens that is disposed in the forward end face of the distal end block at a position facing the exit end face of the light guide fiber bundle in order to enlarge the divergence angle of illuminating light emitted from the light guide fiber bundle.

13 Claims, 6 Drawing Sheets

DISTAL END PART OF ENDOSCOPE

BACKGROUND OF THE INVENTION

The present disclosure relates to subject matter contained in Japanese Patent applications No. 3-191339 (filed on Apr. 26, 1991) and No. 3-206618 (filed on May 14, 1991), which are expressly incorporated herein by reference in their entirety.

1. Field of the Invention

The present invention relates to a distal end part of an endoscope.

It is desirable that the distal end part of an endoscope should be as thin as possible because the thinner the distal end part, the more effectively it can be inserted into a hollow organ of the patient's body, so that the pain inflicted on the patient is minimized. In the case of an endoscope for inspection of the inside of a bronchial tube, for example, it is particularly necessary to minimize the outer diameter of the distal end part because it must be inserted into the inner part of the bronchial tube.

2. Description of the Prior Art

In the distal end part of an endoscope, a light guide fiber bundle for illuminating the observation field of view is disposed in parallel to an objective optical system. An illuminating lens for enlarging the illuminating range is disposed at the exit end of the light guide fiber bundle. In addition, a solid-state imaging device is disposed at a position where an observed image is formed by the objective optical system. These elements are incorporated in a distal end block.

However, the light guide fiber bundle is disposed rather close to the periphery of the distal end block because it extends side by side with the solid-state imaging device, which is thicker than the objective optical system. In the meantime, the diameter of the illuminating lens must be larger than that of the light guide fiber bundle.

Accordingly, the outer edge of the illuminating lens is close to the outer edge portion of the forward end of the distal end block, so that the wall of this portion of the distal end block is exceedingly thin. Therefore, it is likely that the illuminating lens will be readily broken on impact. In addition, since the forward end outer edge portion of the distal end block cannot be rounded satisfactorily but remains edgy, it may cut a mucous membrane in a hollow organ of the patient's body.

In order to prevent such problems, the forward end portion of the distal end block must be thick to a certain extent, resulting in deterioration of the insertability of the endoscope. Thus the endoscope cannot be inserted into a hollow organ of the patient's body effectively and with minimal pains to the patient.

In the meantime, the rear end portion of the distal end block is a thinner than the other portion because it is connected to an insert tube of the endoscope.

Accordingly, if the distal end block is formed as thin as possible, the rear end portion thereof, which is thinner than the other portion, is cut at the outer periphery thereof by a bore for passing built-in parts (i.e., optical fiber bundles, tubes, codes, etc.).

To cope with this problem, it has been conventional practice to cover such a cut portion with the distal end portion of a skin tube used to cover the insert tube.

In actual practice, however, if a skin tube 91 is attached in such a manner that the distal end portion thereof just covers a cut portion 92 of a distal end block 90, as shown in FIG. 7, the mere separation of a narrow bond area 93, between the end face of the skin tube 91 and the distal end block 90, causes water or other liquid to leak in the inside of the endoscope, resulting in a failure to use it.

If the distal end portion of the skin tube 91 is extended as far as the outer peripheral surface of the end portion of the distal end block 90 and bonded to the surface thereof, as shown in FIG. 8, it is possible to cover the cut portion 92 without the likelihood of leakage of water. In FIGS. 7 and 8, reference numeral 95 denotes the foremost one of the joint rings, constituting a bendable portion that is formed at the distal end of the insert tube.

However, if the distal end portion of the skin tube 91 is extended forwardly and bonded to the outer peripheral surface of the distal end block 90, the outer diameter of this portion of the distal end block 90 increases exceedingly, resulting in deterioration of the insertability of the endoscope into a hollow organ of the patient's body.

SUMMARY OF THE INVENTION

An object of the present invention is to provide a distal end part of an endoscope which is designed so that, even if an illuminating lens is attached to the exit end of a light guide fiber bundle, the forward end portion of the distal end block will not increase in outer diameter. There is a very small likelihood that the illuminating lens will be broken.

Another object of the present invention is to provide a distal end part of an endoscope which is designed so that the rear end portion of the distal end block has a relatively small outer diameter, with a very weak likelihood of leakage of water.

Other objects and advantages of the present invention will become apparent from the following detailed description of an illustrated embodiment of the invention.

According to the present invention, there is provided a distal end part of an endoscope having an objective optical system arranged to face forwardly in a distal end block. The object optical system includes a light guide fiber bundle for illuminating an observation field of view of the objective optical system; and a bore that is provided in the distal end block with an angle of inclination so that the bore approaches an optical axis of the objective optical system at the forward end thereof, with the bore receiving an exit end portion of the light guide fiber bundle. The object optical system further includes an illuminating lens that is disposed in the forward end face of the distal end block at a position facing the exit end face of the light guide fiber bundle in order to enlarge the divergence angle of illuminating light emitted from the light guide fiber bundle.

In addition, there is provided a distal end part of an endoscope having an objective optical system arranged to face forwardly in a distal end block, and a solid-state imaging device disposed in the distal end block at a position where an observed image is formed by the objective optical system. The objective optical system includes a light guide fiber bundle for illuminating an observation field of view of the objective optical system; a bore that is provided in the distal end block with an angle of inclination so that the bore approaches an optical axis of the objective optical system at the forward end thereof; and a straight pipe shorter than the objective optical system, which is inserted into the bore and rigidly secured thereto, with the straight pipe receiving an exit end portion of the light guide fiber bundle. The objective optical system further includes illuminating lens that is disposed in the forward end face of the distal end block at a position facing the exit end face of the light guide fiber bundle in order to enlarge the divergence angle of illuminating light emitted from the light guide fiber bundle.

In addition, there is provided a distal end part of an endoscope having a distal end block which is reduced in outer diameter at the rear end portion thereof in order to connect it to the distal end of a flexible insert tube and which is cut at the outer peripheral surface of the thin, rear end portion by a bore for passing built-in parts. The distal end includes a metallic tubular member that is fitted over the outer periphery of the distal end block from the thin rear end portion to a portion having a relatively large outer diameter, which extends forward of the thin rear end portion, and rigidly secured to the portion having a relatively large outer diameter in such a manner that no water will leak in through the joint of the tubular member and the distal end block. The distal end part further includes a skin tube for covering the insert tube, which is rigidly secured at the distal end portion thereof to the outer peripheral surface of the thin rear end portion of the tubular member in such a manner that no water will leak in through the joint of the skin tube and the tubular member.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

One embodiment of the present invention will be described below with reference to the accompanying drawings.

Figure 1:
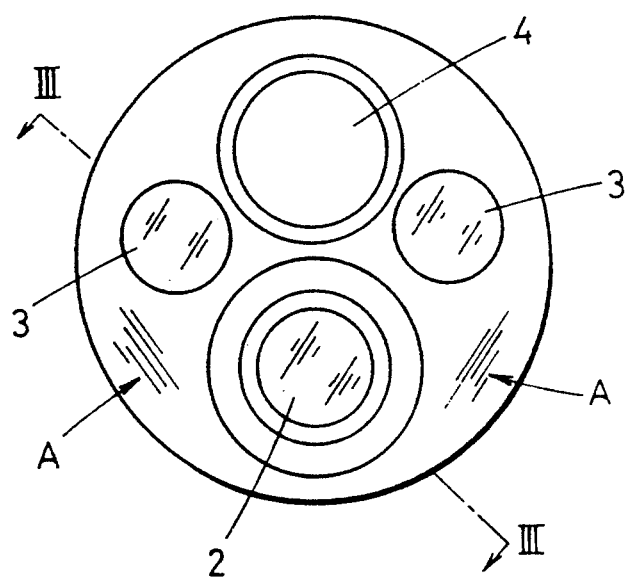
FIG. 1 is front view of one embodiment of the present invention.

FIG. 1 is a front view of a distal end block 1 connected to the distal end of a flexible insert tube of an end-viewing video endoscope. Reference numeral 2 denotes a viewing window, 3 a pair of illuminating windows, and 4 an opening of a biopsy channel also serving as a suction channel.

Figure 2:
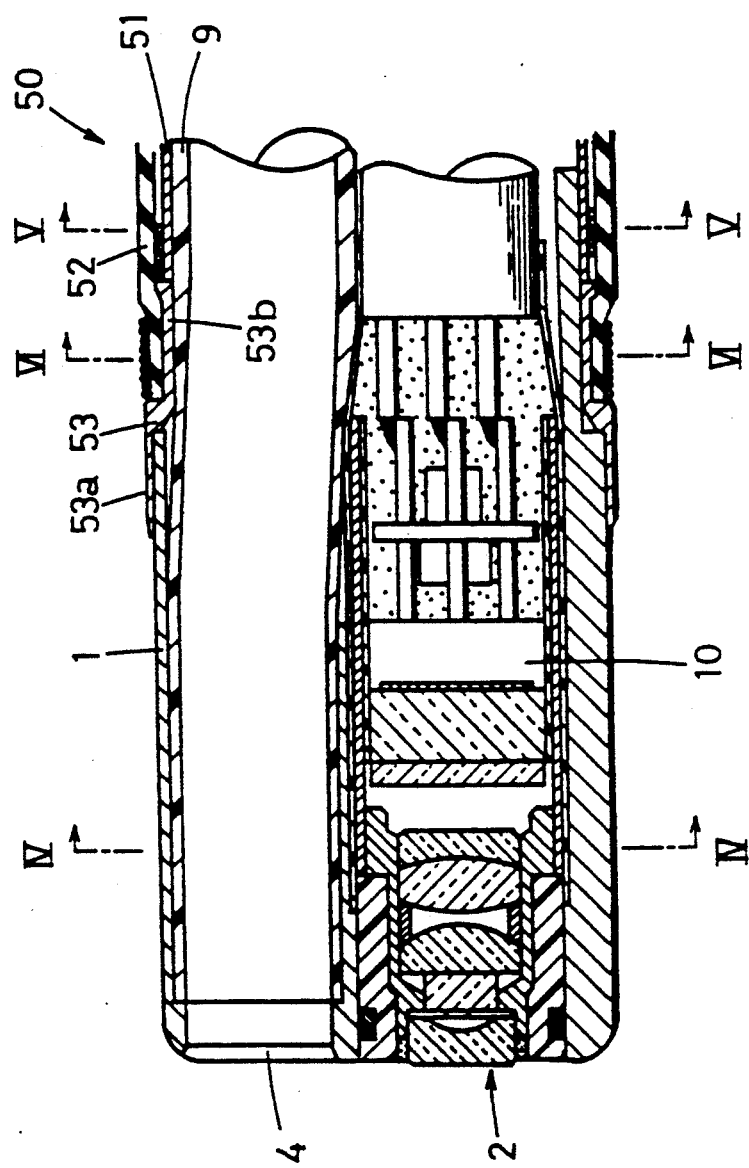
FIG. 2 is a sectional side view of the embodiment of the present invention.
Figure 3:
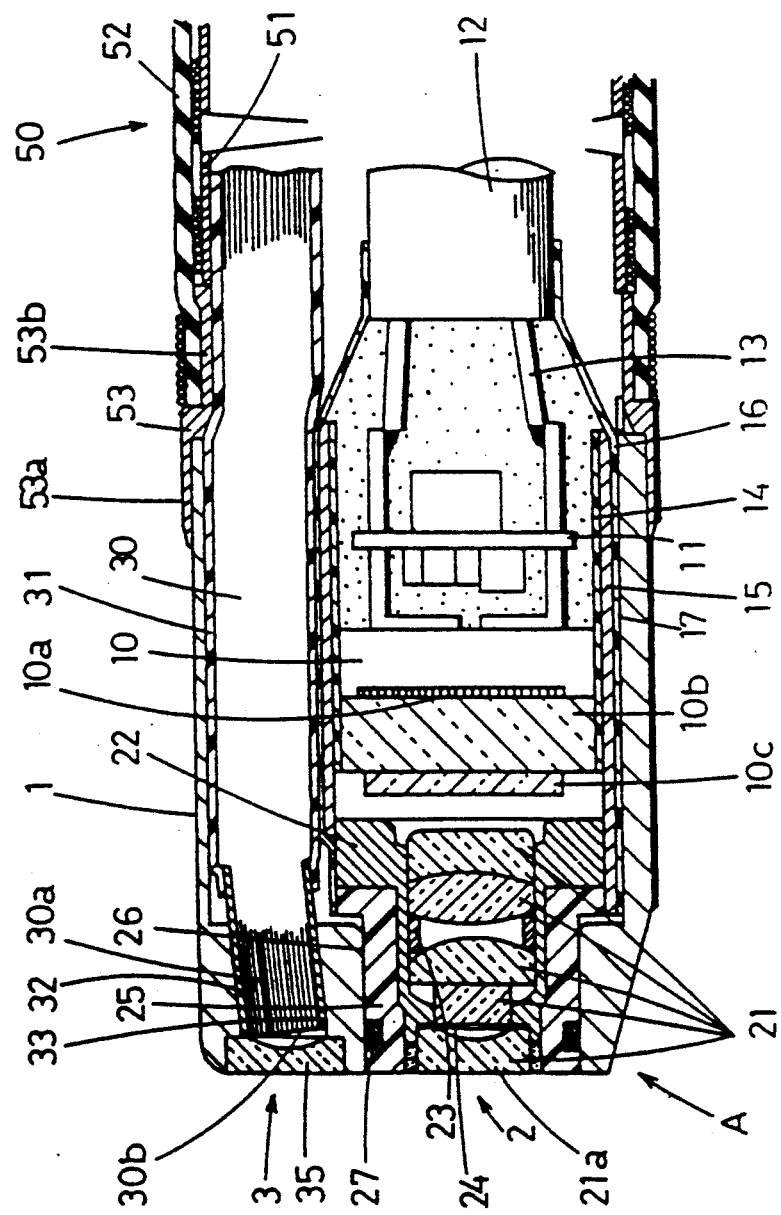
FIG. 3 is a sectional view taken along the line III—III in FIG. 1.

FIG. 2 is a sectional side view showing the distal end block 1 and its vicinities, and FIG. 3 is a sectional view taken along the line III—III in FIG. 1, showing the distal end block 1 and its vicinities, including the viewing and illuminating windows 2 and 3.

A solid-state imaging device 10, which is, for example, a charge-coupled device (CCD), has an image receiving part 10a, a transparent layer 10b made of a transparent epoxy resin material, for example, which is formed on the surface of the image receiving part 10a in order to prevent adhesion of dust to the image receiving part 10a, and a filter 10c for cutting off YAG laser light.

An output signal from the solid-state imaging device 10 is amplified by an electronic circuit formed on a circuit board 11 and then supplied to a monitor device (not shown) through codes 13 extending through a shielded cable 12 after being processed in a signal processing circuit (not shown).

The outer peripheries of the solid-state imaging device 10 and the circuit board 11 are wound with an electrical insulating tape 14 made of a plastic material, for example, and firmly bonded to the inner periphery of a metallic frame 15 through the insulating tape 14. The outer periphery of the frame 15 is also wound with an electrical insulating tape 16.

An objective optical system 21 is arranged to face forwardly in the distal end block 1 to form an observed image on the image receiving part 10a of the solid-state imaging device 10. The objective optical system 21 is firmly bonded to the inside of a metallic lens frame 22. Reference numeral 23 denotes a spacer, and 24 a diaphragm for controlling brightness.

The rear end portion of the lens frame 22 is fitted and bonded to the frame 15 having the solid-state imaging device 10 attached thereto such that the imaging device 10 is disposed at a position where an observed image is formed by the objective optical system 21.

Figure 4:
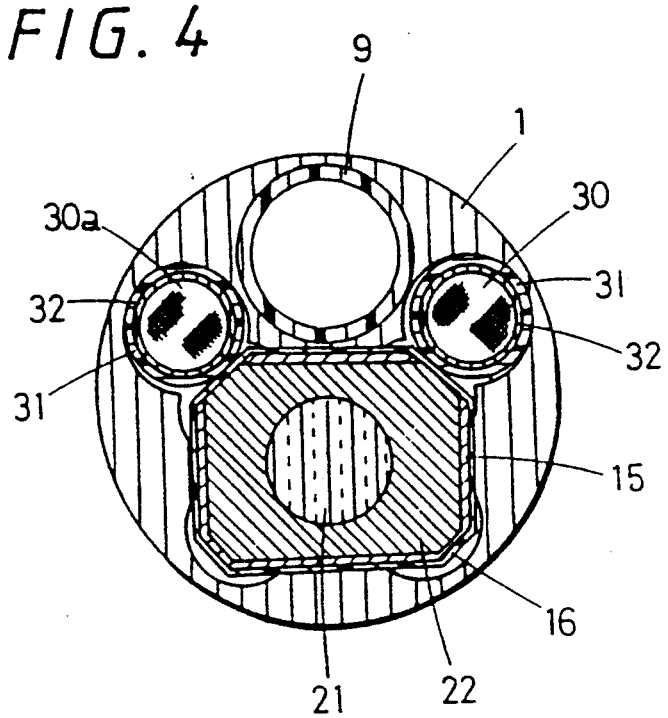
FIG. 4 is a sectional view taken along the line IV—IV in FIG. 2.

The diameter of the solid-state imaging device 10 is much larger than that of the objective optical system 21. Accordingly, the rear end portion of the lens frame 22 is formed in a rectangular cross-sectional configuration which is larger than the cross-section of the forward end half of the lens frame 22 in conformity to the configuration of the frame 15, as shown in FIG. 4, which is a sectional view taken along the line IV—IV in FIG. 2.

A cover lens 21a is bonded to the forward end portion of the lens frame 22 with the brightness diaphragm 24 held therebetween. In this embodiment, the cover lens 21a is a concave lens, which is disposed in the viewing window 2 to constitute a part of the objective optical system 21.

In addition, an electrical insulating member 25, which is formed in the shape of a stepped tube from an electrical insulating plastic material, is fitted onto the periphery of the forward end portion of the lens frame 27, so as to surround it and firmly bonded thereto by using a deaerated epoxy adhesive.

The outer periphery of the electrical insulating member 25 is fitted into a bore 26 provided in the distal end block 1, with an electrical insulating O-ring 27 interposed between the two members to seal the gap therebetween, so that no water will leak in through the gap.

Figure 5:
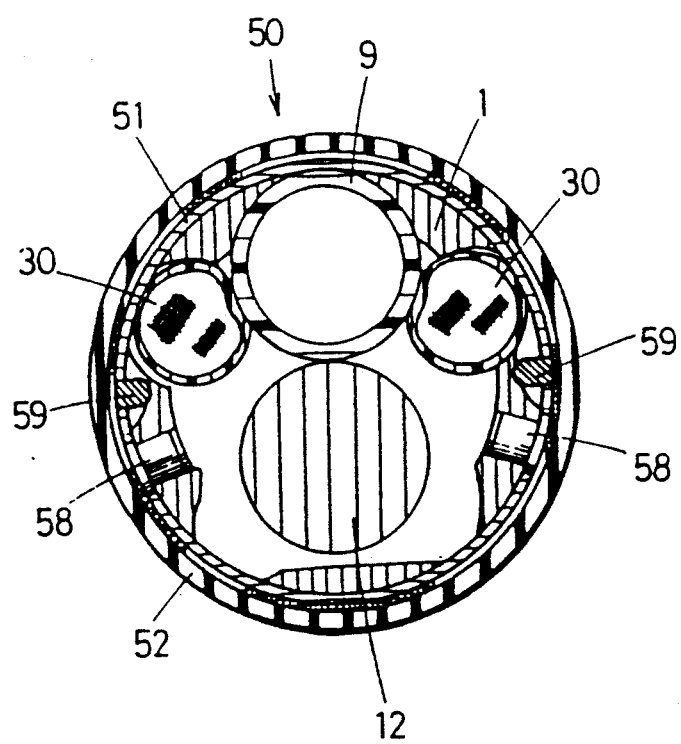
FIG. 5 is a sectional view taken along the line V—V in FIG. 2.

A pair of light guide fiber bundles 30, for illuminating the observation field of view, are inserted into the insert part of the endoscope over the entire length thereof and covered with respective flexible silicone rubber tubes 31. In the distal end block 1, each light guide fiber bundle 30 extends in a slightly flattened, state in parallel to the frame 15, as shown in FIG. 5, having the solid-state imaging device 10 attached thereto, at a position rather close to the periphery of the distal end block 1.

The exit end portion 30a of each light guide fiber bundle 30 is inserted into a short, straight metallic pipe 32 and bonded thereto with an adhesive poured into the gap therebetween.

The distal end block 1 is provided with bores 33 for fitting the metallic pipes 32, respectively. The bores 33 are inclined inwardly toward the viewing window 2 so as to approach the optical axis of the objective optical system 21 at the forward end thereof by making use of the fact that the objective optical system 21 is thinner than the solid-state imaging device 10, and there is therefore a space around the objective optical system 21. The angle of inclination of the bores 33 is of the order of 3 degrees to 15 degrees, for example, with respect to the axis of the distal end block 1.

The metallic pipes 32 are fitted into and firmly bonded to the respective bores 33, thereby directing illuminating light toward the viewing window 2.

It should be noted that the forward end portion of the frame 15, having the solid-state imaging device 10 attached thereto, is cut at portions thereof which are close to the metallic pipes 32 of the light guide fiber bundles 30 so that these portions will not interfere with the metallic pipes 32, as shown in FIGS. 3 and 4.

The overall length of each straight metallic pipe 32 is shorter than that of the objective optical system 21, so that the pipe 32 can be inclined without any problem. Thus, the rear end portion of the metallic pipe 32 will not project outwardly. The forward end portion of the distal end block 1 can be formed with a minimal outer diameter.

An illuminating lens 35, which is a concave lens, is firmly bonded to the forward end face of the distal end block 1 at the position of each illuminating window 3, that is, at a position which faces the exit end face 30b of each light guide fiber bundle 30, so that the divergence angle of illuminating angle is enlarged by the illuminating lens 35.

Since the exit end portion 30a of the light guide fiber bundle 30 is inclined inwardly, the illuminating lens 35 is disposed rather close to the center of the end face of the distal end block 1.

Thus, since the outer edge portion of the illuminating lens 35 is separate from the outer edge portion of the distal end block 1, the forward end portion of the distal end block 1 need not be increased in outer diameter. It is also possible to round the forward end outer edge portion of the distal end block 1 to a substantial degree.

It should be noted that forward end portions (denoted by A in FIGS. 1 and 3) of the distal end block 1 where no built-in parts are present are cut off taperingly with a view to improving the insertability.

As shown in FIG. 2, the distal end of a biopsy channel tube 9 made of a fluorocarbon resin material, for example, is bonded to the distal end block 1 in communication with the opening 4. The biopsy channel tube 9 has a relatively large wall thickness inside a bendable portion 50, while inside the distal end block 1, which is nonbendable, the biopsy channel tube 9 has a relatively small wall thickness. At the boundary therebetween, the wall thickness of the biopsy channel tube 9 varies gradually.

The bendable portion 50 is formed at the distal end of the insert tube of the endoscope such that it can be bent by remote control. The foremost joint ring 51 of the bendable portion 50 is connected to the rear end portion of the distal end block 1 by connecting pins 58, as shown in FIG. 5, which is a sectional view taken along the line V—V in FIG. 2.

Figure 6:
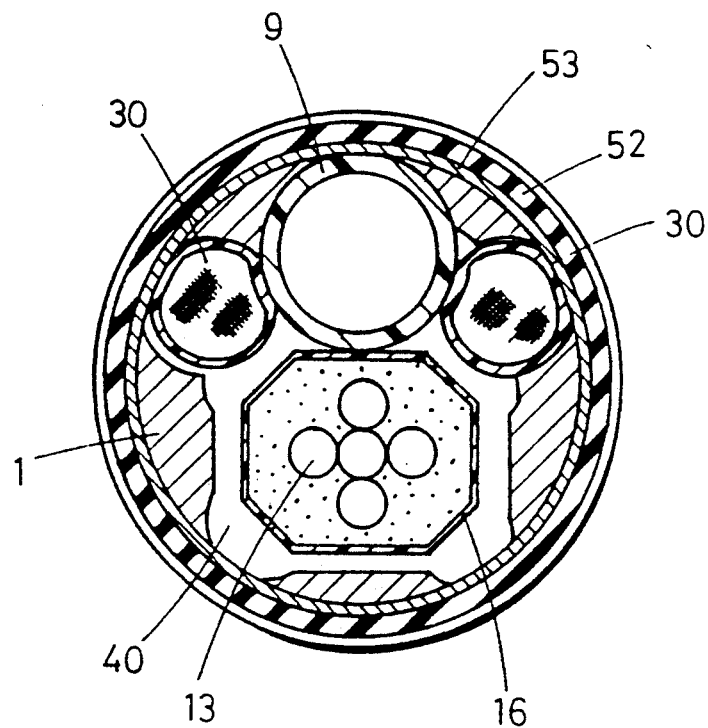
FIG. 6 is a sectional view taken along the line VI—VI in FIG. 2.
Figure 7:
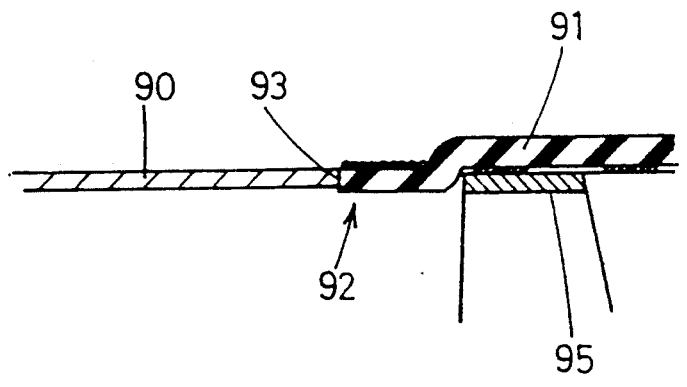
FIG. 7 is a fragmentary sectional side view showing a distal end part of an endoscope according to the prior art.
Figure 8:
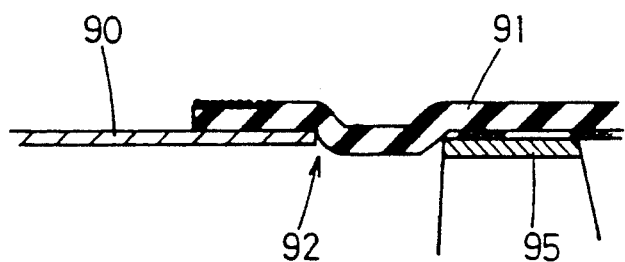
FIG. 8 is a fragmentary sectional side view showing a distal end part of an endoscope according to another prior art device.

The rear end portion of the distal end block 1 has an outer diameter smaller than that of the forward end portion thereof so as to be connected to the bendable portion 50, as stated above. As a result, the outer peripheral surface of the rear end portion of the distal end block 1 is cut by the outer edge of a bore provided in the distal end block 1 for passing various built-in parts (i.e., the light guide fiber bundles 30, the codes 13, the biopsy channel tube 9, etc.) rearwardly from the distal end block 1, as shown in FIG. 6, which is a sectional view taken along the line VI—VI in FIG. 2.

However, the outer peripheral surface of the distal end block 1 is not cut at the portion thereof which has a larger outer diameter than that of the rear end portion, so that the inside and outside of the distal end block 1 are completely isolated from each other, as shown in FIG. 4.

As shown in FIGS. 2 and 3, a stepped tubular member 53 is fitted over the outer periphery of the distal end block 1 from the rear end portion having a relatively small outer diameter to a portion having a relatively large outer diameter which extends forward of it. The tubular member 53 comprises a relatively thick forward end portion 53a and a relatively thin rear end portion 53b. The inner surface of the thick forward end portion 53a is firmly bonded to the outer surface of the distal end block 1 in such a manner that no water will leak in through the joint of the tubular member 53 and the distal end block 1. The thin rear end portion 53b externally covers the cut portions at the rear end of the distal end block 1.

In addition, the distal end portion of a skin tube 52, made of a stretchable rubber material for covering the bendable portion 50, is secured to the outer surface of the thin portion 53b of the tubular member 53 by bonding and binding in such a manner that no water will leak in through the joint of the skin tube 52 and the tubular member 53. In this case, the distal end of the skin tube 52 does not reach the outer surface of the thick portion 53a of the tubular member 53.

The tubular member 53 is made of a metallic material, for example, stainless steel, so that the wall thickness thereof can be reduced by a large margin, for example, to about one third of that of the skin tube 52. Accordingly, it is possible to provide the tubular member 53 without an increase in the outer diameter of the distal end part of the endoscope. However, in the figures, the wall thickness of the tubular member 53 is shown to be a little larger than the actual one, for the purpose of showing the tubular member 53 clearly.

The bond area for preventing the leakage of water from the outside into the inside of the distal end block 1 is formed between the inner surface of the thick portion 53a of the tubular member 53 and the outer peripheral surface of the distal end block 1, and also between the outer surface of the thin portion 53b of the tubular member 53 and the inner surface of the skin tube 52. Accordingly, it is possible to obtain an ample bond area for either of the joints, and hence possible to minimize the likelihood of leakage of water due to separation of the bonded portions.

According to the present invention, each illuminating lens can be disposed at a position which is away from the outer edge portion of the distal end block and rather close to the center thereof, and it is therefore possible to reduce the outer diameter of the forward end portion of the distal end block. Thus, the insertability of the endoscope is improved. Since the forward end outer edge portion of the distal end block can be rounded to a substantial degree, it is possible to reduce the likelihood that the distal end block will damage a mucous membrane in a hollow organ of the patient's body.

Since the illuminating lens is disposed rather close to the center of the distal end block, it will be not readily broken on impact. Thus, the durability improves, and the illuminating condition for an object at a short distance also improves.

In addition, according to the present invention, a metallic tubular member is tightly fitted over the rear end portion of the distal end block from a relatively thin portion which is cut at the outer periphery thereof to a relatively thick portion with no cut which extends forward of it in such a manner that no water will leak in through the joint of the tubular member and the distal end block. The distal end portion of a skin tube is firmly secured to the outer peripheral surface of a thin portion of the tubular member in such a manner that no water will leak in through the joint between the skin tube and the tubular member. Accordingly, the rear end portion of the distal end part of the endoscope can be reduced in outer diameter, and it is also possible to reduce markedly the likelihood of leakage of water.

While the invention has been described by reference to a specific embodiment chosen for purposes of illustration, it should be apparent that numerous modifications could be made thereto by those skilled in the art without departing from the basic concept and scope of the invention.

I claim:

1. A distal end part of a forward view type endoscope having an objective optical system arranged to face forwardly in a distal end block, comprising:
    a light guide fiber bundle, positioned adjacent a periphery of said distal end block, for illuminating an observation field of view of said objective optical system;
    a bore that is provided in said distal end block with an angle of inclination, so that said bore approaches an optical axis of said objective optical system at a forward end thereof, said bore receiving an exit end portion of said light guide fiber bundle; and
    an illuminating lens, having a diameter which is larger than a diameter of said bore, said illuminating lens disposed in a forward end face of said distal end block at a position facing an exit end face of said light guide fiber bundle in order to enlarge a divergence angle of illuminating light emitted from said light guide fiber bundle, whereby said illuminating lens can be positioned in said forward end face of said distal end block such that said illuminating lens does not protrude out of the periphery of said distal end block.

2. A distal end part of forward view type endoscope having an objective optical system arranged to face forwardly in a distal end block, and a solid state imaging device disposed in said distal end block at a position where an observed image is formed by said objective optical system, comprising:
    a light guide fiber bundle, positioned adjacent a periphery of said distal end block, for illuminating an observation field of view of said objective optical system;
    a bore that is provided in said distal end block with an angle of inclination, so that said bore approaches an optical axis of said objective optical system at a forward end thereof;
    a straight pipe, shorter than said objective optical system, which is inserted into said bore and rigidly secured thereto, said straight pipe receiving an exit end portion of said light guide fiber bundle; and
    an illuminating lens, having a diameter which is larger than a diameter of said bore, said illuminating lens disposed in a forward end face of said distal end block at a position facing an exit end face of said light guide fiber bundle in order to enlarge a divergence angle of illuminating light emitted from said light guide fiber bundle, whereby said illuminating lens can be positioned at a forward end face of said distal end block such that said illuminating lens does not protrude out of the periphery of said distal end block.

3. A distal end part of an endoscope according to claim 2, wherein said light guide fiber bundle is disposed in a slightly flattened state inside the distal end block, said slightly flattened state defined by a portion of a periphery of said light guide fiber bundle being noncircular said light guide fiber bundle disposed, in parallel to a frame having said solid state imaging device attached thereto.

4. A distal end part of an endoscope according to claim 2, wherein the exit end portion of said light guide fiber bundle is bonded to an inside of said pipe by using an adhesive.

5. A distal end part of an endoscope according to claim 2, wherein said bore is inclined at an angle in a range of 3 degrees to 15 degrees with respect to a longitudinal axis of said distal end block.

6. A distal end part of an endoscope according to claim 2, wherein said illuminating lens is a concave lens.

7. A distal end part of an endoscope according to claim 2, wherein the forward end portion of said distal end block is at least partly tapered.

8. The distal end part of a forward view endoscope according to claim 1, said illuminating lens comprising means for enlarging a divergence angle of illuminating light emitted from said light guide fiber bundle.

9. The distal end part of a forward view endoscope according to claim 2, said illuminating lens comprising means for enlarging a divergence angle of illuminating light emitted from said light guide fiber bundle.

10. The distal end part of a forward view type endoscope according to claim 1, further comprising:
    a metallic tubular member that is fitted over an outer periphery of said distal end block, from a thin rear end portion of said distal end block, to a portion having a relatively large outer diameter, said tubular member extending forwardly of said thin rear end portion, and rigidly secured to said portion having a relatively large outer diameter, in such a manner that no water will leak in through a joint of said tubular member and said distal end block; and
    a skin tube for covering a flexible insert tube, which is rigidly secured at a distal end portion, to an outer peripheral surface of the thin rear end portion of said tubular member, in such a manner that no water will leak through a joint of said skin tube and said tubular member.

11. The distal end part of an endoscope according to claim 10, wherein said skin tube is a stretchable tube for covering a bendable portion which can be bent by remote control.

12. The distal end part of a forward view type endoscope according to claim 2, further comprising:

a metallic tubular member that is fitted over an outer periphery of said distal end block, from a thin rear end portion of said distal end block, to a portion having a relatively large outer diameter, said tubular member extending forwardly of said thin rear end portion, and rigidly secured to said portion having a relatively large outer diameter, in such a manner that no water will leak in through a joint of said tubular member and said distal end block; and a skin tube for covering a flexible insert tube, which is rigidly secured at a distal end portion, to an outer peripheral surface of the thin rear end portion of said tubular member, in such a manner that no water will leak through a joint of said skin tube and said tubular member.

13. The distal end part of an endoscope according to claim 12, wherein said skin tube is a stretchable tube for covering a bendable portion which can be bent by remote control.

* * * * *

UNITED STATES PATENT AND TRADEMARK OFFICE
CERTIFICATE OF CORRECTION

PATENT NO. : 5,305,736
DATED : April 26, 1994
INVENTOR(S) : Keiji ITO

It is certified that error appears in the above-indentified patent and that said Letters Patent is hereby corrected as shown below:

On the cover, in section [57], "ABSTRACT", line 9, change "boar" to ---bore---.

At column 10, line 5 (claim 12, line 16) insert ---in--- after "leak".

Signed and Sealed this

Twenty-sixth Day of September, 1995

Attest:

BRUCE LEHMAN

Attesting Officer    Commissioner of Patents and Trademarks